United States Patent [19]

Tokuda et al.

[11] Patent Number: 4,879,221

[45] Date of Patent: Nov. 7, 1989

[54] PROCESS FOR DETERMINATION OF γ-GTP ACTIVITY

[75] Inventors: Kuniaki Tokuda; Seiji Morii, both of Kawagoe; Kazuhiko Yamanishi, Tokyo, all of Japan

[73] Assignee: Wako Pure Chemical Industries, Ltd., Osaka, Japan

[21] Appl. No.: 902,897

[22] Filed: Sep. 2, 1986

[51] Int. Cl.$^4$ .................... C12Q 1/48; G01N 31/00
[52] U.S. Cl. ........................ 435/15; 435/188; 435/193; 435/810; 435/24; 436/18; 436/176
[58] Field of Search ............ 435/24, 23, 15, 188, 435/193, 810; 436/176, 18

[56] References Cited

U.S. PATENT DOCUMENTS

| | | | |
|---|---|---|---|
| 3,453,258 | 7/1969 | Parmerter et al. | 260/209 |
| 3,453,259 | 7/1969 | Parmerter et al. | 260/209 |
| 4,511,651 | 4/1985 | Beaty et al. | 435/15 |
| 4,596,795 | 6/1986 | Pitha | 514/58 |

OTHER PUBLICATIONS

"Inclusion of Aromatic Compounds by a β-Cyclodextrin–Epichlorohydrin Polymer", Harada et al., 2257 Polymer Journal, vol. 13, (1981), Aug., No. 8, Tokyo, Japan.
Patent Abstracts of Japan, vol. 10, No. 144, JP-A-61 13 99.
Patent Abstracts of Japan, vol. 9, No. 311, JP-A-60 160 896.

*Primary Examiner*—Robert J. Warden
*Assistant Examiner*—Toni R. Scheiner
*Attorney, Agent, or Firm*—Armstrong, Nikaido, Marmelstein, Kubovcik & Murray

[57] ABSTRACT

γ-GTP activity can be determined easily by using a stabilized substrate solution comprising γ-L-glutamyl-p-nitroanilide and a modified cyclodextrin, together with an acceptor solution containing an acceptor for glutamic acid and measuring p-nitroaniline generated.

9 Claims, No Drawings

PROCESS FOR DETERMINATION OF γ-GTP ACTIVITY

BACKGROUND OF THE INVENTION

This invention relates to a process for determination of γ-glutamyl transpeptidase activity using γ-L-glutamyl-p-nitroanilide as a substrate.

Determination of γ-glutamyl transpeptiase (hereinafter referred to as "γ-GTP⇌") activity is widely used for clinical diagnosis of hepatoiliary duct disease, screening of drinkers, and the like. Among various methods for determining γ-GTP activity, a method using γ-L-C-glutamyl-p-nitroanilide as a substrate is most popular and employed widely. But γ-L-glutamyl-p-nitroanilide is remarkably poor in solubility at near neutral pH, which is most suitable for the stabilization of substrate and enzymatic reaction. Thus, there is generally employed a so-called acid dissolution method wherein γ-L-glutamyl-p-nitroanilide is sufficiently dissolved at a low pH having relatively higher solubility and mixed with a buffer solution of near neutral (pH=about 8.5) at the time of use. But since a strong acid used for the dissolution hydrolyzes this substrate so as to raise the blank value gradually, a usable period of the formulation is about 5 hours after the preparation.

In order to improve the solubility of this substrate, various methods have been proposed and used practically as follows: (1) A method wherein a cationic surface active agent or anionic surface active agent is added to this substrate to improve the solubility of this substrate in water and an inhibitory action for the γ-GTP activity by such an ionic surface active agent is relaxed by a nonionic surface active agent. (2) A method wherein a water-soluble group such as a —CO₂H group, —SO₃H group, or the like is provided at an ortho position relative to the —NO₂ group of this substrate to improve the regarding solubility of this substrate in water. (3) A method wherein the solubility of this substrate in water is improved by applying clathrating force of cyclodextin (Japanese Patent Unexamined Publication No. 74099/82).

But these methods have various disadvantages. For example, according to the method (1) using a surface active agent, the inhibitory action of the ionic surface active agent for γ-GTP is so strong that the recovery rate of γ-GTP activity is about 70 to 80% even if a nonionic surface active agent is added. Further, by the addition of the surface active agent, the absorption of hemoglobin changes with the lapse of time and the absorption of 410 nm used for tracing the generating rate of p-nitroaniline is reduced with the lapse of time, so that a negative error is consequently given to the measured value of γ-GTP activity. According to the method (2) for providing a water-soluble group, there are various problems in that measured values of γ-GTP activity are higher than the true values, the substrate in a formulation solution is denatured in several days after the preparation to lower measured values of γ-GTP activity, and sometimes a precipitate due to the denaturing is deposited. Further, according to the method (3) for applying the clathrating force of cyclodextrin, there is no problem of influence of hemoglobin and variation of measured values of γ-GTP activity. But since the improvement of the solubility in water is insufficient, when a substrate solution containing cyclodextrin as a clathrating reagent is freeze dried, the concentration of the solution for preparations is that of the final use or twice of that at most.

In order to improve such a disadvantage of using cyclodextrin, there are proposed the use of modified cyclodextrins in place of cyclodextrin (Japanese Patent Unexamined Publication Nos. 160896/85 and 1399/86). According to Japanese Patent Unexamined Publication No. 160896/85, there are used cyclodextrins modified by introducing water-soluble groups such as $NO_2$, $PO_3H$, $SO_3H$, $COOH$, etc. into the positions of hydroxyl groups. The solubility of the modified cyclodextrins at room temperature is improved, but clathrating force by the modified cyclodextrins at low temperatures is insufficient and crystals are deposited when allowed to stand at low temperatures for a long period of time. On the other hand, according to Japanese Patent Unexamined Publication No. 1399/86 wherein the hydroxyl groups of cyclodextrin is replaced by methyl groups, freeze dried products are poor in stability and reagent blank values rise when the modified cyclodextrins are used after being stored at room temperature for a long period of time.

On the other hand, as to a mechanism for forming clathrate compounds, there has been proposed a participation of various intermolecular force. It seems that a part or whole of various intermolecular forces such as dispersion force, interdipole force, hydrogen bond, hydrophobic bond, charge transfer force, etc., is involved in the formation of cyclodextrin clathrate compound. Therefore, if chemical structures of molecules are different, mechanisms for forming clathrate compounds are naturally different. Further, even if a clathrate compound is formed, there is a fear of suppressing the enzymatic reaction by making the whole of γ-L-glutamyl-p-nitroanilide which is a guest molecule or active site for enzymatic reaction with γ-GTP clathrated in the cyclodextrin cavity which is the host molecule. Therefore, even if γ-L-glutamyl-p-nitroanilide is clathrated by cyclodextrin, it is impossible to expect whether other cyclodextrin derivatives can clathrate γ-L-glutamyl-p-nitroanilide or not. Even if γ-L-glutamyl-p-nitroanilide can be clathrated by the other cyclodextrin derivatives, it is impossible to expect whether the clathrated γ-L-glutamyl-p-nitroanilide maintains a function as the substrate for γ-GTP or not.

SUMMARY OF THE INVENTION

It is an object of this invention to provide a process for determination of γ-GTP activity with ease by solving the problem of solubility of γ-L-glutamyl-p-nitroanilide used as a substrate.

This invention provides a process for determining γ-GTP activity which comprises adding to a sample a substrate solution comprising γ-L-glutamyl-p-nitroanilide, and a modified cyclodextrin of the formula:

$$\beta-CD(-OH)_{21-x}[-OC_nH_{2n-(m-1)}(-OH)_m]_x \quad (I)$$

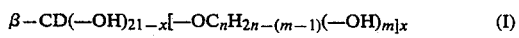

wherein CD is a cyclodextrin residue; m is an integer of 1 to 10; n is an integer of 1 to 5, provided that $2n-(m-1) \geq 0$; and x is 3 to 21, or a modified cyclodextrin of the formula:

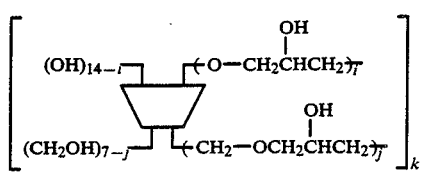

(II)

wherein i is zero to 3; j is 1 to 5; and k is 2 to 5, and adding to the sample an acceptor solution containing an acceptor for glutamic acid, in this order or a reverse order, and measuring p-nitroaniline generated.

DESCRIPTION OF THE PREFERRED EMBODIMENTS

The process of this invention is characterized by using the special modified cyclodextrin of the formula (I) or (II) in the determination of γ-GTP activity by using γ-L-glutamyl-p-nitroanilide as a substrate. The modified cyclodextrin of the formula (I) or (II) effectively clathrates γ-L-glutamyl-p-nitroanilide and the resulting clathrate compound does not suppress γ-GTP activity. By using γ-L-glutamyl-p-nitroanilide as the substrate in the presence of the modified cyclodextrin, not only the solubility of the substrate is remarkably improved, but also the determination of γ-GTP activity becomes easy.

According to this invention, it is important that the special modified cyclodextrin of the formula (I) or (II) and γ-L-glutamyl-p-nitroanilide are present in the enzymatic reaction system of γ-GTP. The measuring step of γ-GTP activity itself can be conducted by using a conventional method wherein the reaction is carried out in a conventionally used buffer solution (e.g. tris(hydroxymethyl)aminomethane (Tris)-HCl buffer solution, etc.) in the presence of an acceptor for glutamic acid such as glycylglycine, etc. Then, absorbance of p-nitroaniline generated by the action of γ-GTP is measured by an initial rate measuring method (a one point assay, a rate assay, etc.) wherein the absorbance is directly measured, a method wherein a color is produced by adding a p-dialkylaminobenzaldehyde, p-dialkylaminocinnamaldehyde, or the like thereto and its absorbance is measured by a conventional method. For example, the absorbance can be measured by using a conventional buffer solution (e.g. 0.1M Tris-HCl buffer), making the pH of the reaction solution 7.5 to 8.5, using the substrate in an amount of 3 to 8 mmol/liter and an acceptor (e.g. glycylglycine) in an amount of 20 to 100 mmol/liter at the measuring temperature of 25° to 37° C. using a wavelength of 404 to 415 nm or 450 to 550 nm.

The modified cyclodextrin can be represented by the formula:

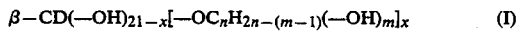

$$\beta-CD(-OH)_{21-x}[-OC_nH_{2n-(m-1)}(-OH)_m]_x \quad (I)$$

wherein CD is a cyclodextrin residue obtained by removing all the hydroxyl groups; m is an integer of 1 to 10, preferably 1 to 5; n is an integer of 1 to 5, preferably 2 to 4, provided that $2n-(m-1)\geq 0$; and x is 3 to 21, preferably 5 to 21, and more preferably 7 to 18.

Examples of the modified cyclodextrin of the formula (I) are heptakis-(6-O-hydroxypropyl)-β-cyclodextrin, heptakis-(6-O-1,3-dihydroxypropyl)-β-cyclodextrin, heptakis-(2,6-di-O-hydroxyethyl)-β-cyclodextrin, pentakis-(6-O-hydroxymethyl)-β-cyclodextrin, tetrakis-(2,6-O-hydroxymethyl)-β-cyclodextrin, heneicosakis-(2,3,6-O-hydroxy-methyl)-β-cyclodextrin, pentakis-(6-O-hydroxyethyl)-β-cyclodextrin, heptakis-(6-O-hydroxyethyl)-β-cyclodextrin, tetradekakis-(2,6-O-hydroxyethyl)-β-cyclodextrin, heneicosakis-(2,3,6-O-hydroxyethyl)-β-cyclodextrin, pentakis-(6-O-hydroxypropyl)-β-cyclodextrin, heptakis-(6-O-hydroxypropyl)-β-cyclodextrin, tetradekakis-(2,6-O-hydroxypropyl)-β-cyclodextrin, heneicosakis-(2,3,6-O-hydroxypropyl)-β-cyclodextrin, pentakis-(6-O-hydroxybutyl)-β-cyclodextrin, heptakis-(6-O-hydroxybutyl)-β-cyclodextrin, tetradekakis-(2,6-O-hydroxybutyl)-β-cyclodextrin, heneicosakis-(2,3,6-O-hydroxybutyl)-β-cyclodextrin, pentakis-(6-O-hydroxyhexyl)-β-cyclodextrin, heptakis-(6-O-hydroxyhexyl)-β-cyclodextrin, tetradekakis-(2,6-O-hydroxyhexyl)-β-cyclodextrin, heneicosakis-(2,3,6-O-hydroxyhexyl)-β-cyclodextrin, keptakis-(6-O-dihydroxymethyl)-β-cyclodextrin, heptakis-[6-O-(1,2-dihydroxyethyl)]-β-cyclodextrin, heptakis-[6-O-(2,2-dihydroxyethyl)]-βcyclodextrin, heptakis-[6-O-(1,2,2-trihydroxypropyl)]-β-cyclodextrin, heptakis-[6-O-(2,3,3-trihydroxypropyl)]-βcyclodextrin, heptakis-[6-O-(2,2,3,3-tetrahydroxybutyl)]-βcyclodextrin, heptakis-[6-O-(2,2-dihydroxypsec-butyl)]-βcyclodextrin, heptakis-(6-O-hydroxy-sec-butyl)-β-cyclodextrin, etc.

The modified cyclodextrin can also be represented by the formula:

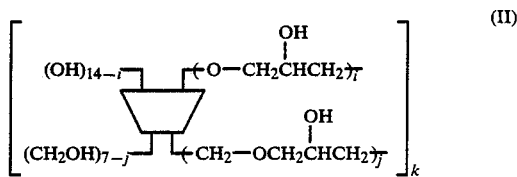

(II)

wherein i is zero to 3; j is 1 to 5; and k is 2 to 5.

Examples of the modified cyclodextrin of the formula (II) are β-cyclodextrin-epichlorohydrin condensates having a molecular weight of 2416 to 5000, etc.

These modified cyclodextrin can be produced by the methods disclosed, for example, in U.S. Pat. Nos. 3,453,258 and 3,453,259, and Polymer Journal, vol. 13, No. 8 pp777-781 (1981).

The measured values of γ-GTP activity obtained by the process of this invention has good correlation to those obtained by the acid dissolution method and there is no problem as to influence of hemoglobin and variation of γ-GTP activity values compared with the prior art methods (1), (2) and (3) mentioned above. By the use of the special modified cyclodextrin, γ-L-glutamyl-p-nitroanilide (γ-L-G-p-N) is remarkably effectively clathrated to improve the solubility thereof remarkably and to improve the stability of substrate solution after dissolution. Further γ-GTP activity is not influenced by the use of special modified cyclodextrin and thus measured values of γ-GTP activity can easily be obtained. Further, by using the special modified cyclodextrin, not only the solubility of γ-L-glutamyl-p-nitroanilide is improved surprisingly to 150 mM at 0° C. but also the solubility at low temperatures is remarkably improved, which results in making freeze drying of a condensed substrate solution for giving solid reagents very easy. The freeze dried product can be stored stably for a long period of time.

Comparison in various properties is made as to the prior art method and the process of this invention and listed in Table 1.

TABLE 1

| Method | Substrate | Dissolution method | Solubility in water | Measured value of γ-GTP in serum | Influence of haemolysis (hemoglobin 1000 mg/dl) | Stability after dissolution |
|---|---|---|---|---|---|---|
| Acid dissolution method | γ-L-G-p-N | Acid (0.1 N) | 20 mM | 100 (standard) | −3 mIU | 20° C.-5 hr 5° C.-crystal deposition |
| (1) Surface active agent method | γ-L-G-p-N | Cationic surfactant Nonionic surfactant | 5 mM | 72 | −16 mIU | 20° C.-2 days 5° C.-7 days (partial crystal deposition) |
| | γ-L-G-p-N | Anionic surfactant Nonionic surfactant | 5 mM | 68 | −19 mIU | 20° C.-2 days 5° C.-7 days (partial crystal deposition) |
| (2) Water-soluble substrate method | γ-L-G-p-N m-carboxylic acid | — | ≧300 mM | 115 | −4 mIU | 20° C.-2 days 5° C.-3 days |
| | γ-L-G-p-N m-sulfonic acid | — | ≧300 mM | 160 | −3 mIU | 20° C.-2 days 5° C.-3 days |
| (3) CD method | γ-L-G-p-N | Cyclodextrin | 16 mM | 99 | −3 mIU | 20° C.-2 days 5° C.-4 days |
| Method of this invention | γ-L-G-p-N | β-CD hydroxyethyl derivative (I) (m=1, n=2, x=7) | 250 mM | 109 | −3 mIU | 20° C.-3 days 5° C.-10 days |
| | γ-L-G-p-N | β-CD hydroxypropyl derivative (I) (m=1, n=3, x=7) | 250 mM | 98 | −3 mIU | 20° C.-3 days 5° C.-10 days |
| | γ-L-G-p-N | β-CD dihydroxypropyl derivative (I) (m=2, n=3, x=7) | 200 mM | 97 | −2 mIU | 20° C.-3 days 5° C.-10 days |
| | γ-L-G-p-N | β-CD epichlorohydrin condensate (II) (k ≈ 2, i + j ≈ 4) | 200 mM | 102 | −3 mIU | 20° C.-3 days 5° C.-10 days |

Note γ-L-G-p-N = γ-L-glutamyl-p-nitroanilide

For practicing the process of this invention, a sample is treated with the substrate solution comprising γL-glutamyl-p-nitroanilide.

As the sample, there can be used serum or blood.

The modified cyclodextrin is used in the substrate solution in an amount of 1.2 to 5.0 moles per mole of γ-L-glutamyl-p-nitroanilide.

The treatment of the sample by the substrate solution is usually conducted at 25°–37° C. for 1 to 5 minutes (preincubation).

Then, the solution containing an acceptor for glutamic acid such as glycylglycine, etc, is added to the resulting sample solution and incubated at 25°–37° C. for 0 to 2 minutes.

The generated p-nitroaniline is measured by spectrophotometry using a conventional method.

This invention is illustrated by way of the following Examples.

EXAMPLE 1

[Preparation of Reagent Solutions]

① Substrate buffer solution

A 0.1M Tris-HCl buffer solution (pH 8.40) was prepared by dissolving heptakis-(6-O-hydroxypropyl)-β-cyclodextrin (m=1, n=3 and x=7 in the formula (I)) so as to make the concentration 10 mmol/liter and γ-L-glutamyl-p-nitroanilide so as to make the concentration 5 mmol/ liter.

② Glycylglycine solution

To glycylglycine in an amount of 162 mmol/liter sodium hydroxide was added so as to make the pH 8.40.

[Procedure]

To 50 μl of sample (serum), 2.0 ml of the substrate buffer solution was added and incubated at 37° C. for 3 minutes. Subsequently, 0.5 ml of the glycylglycine solution was added to the resulting solution and mixed well. Then, an increase of absorbance at 410 nm of p-nitroaniline generated was measured by using a spectrophotometer to calculate γ-GTP activity value as follows:

$$\delta\text{-GTP activity value } (mIU) = \frac{\Delta E/\min \times 1 \times 2.55 \times 1000}{8.8 \times 10^6 \times 10^{-6} \times 0.05}$$

wherein ΔE/min means an increase of absorbance per unit time (1 minute).

REFERENCE EXAMPLE 1 (ACID DISSOLUTION METHOD)

[Preparation of Reagent Solutions]

① Substrate solution

γ-L-Glutamyl-p-nitroanilide was dissolved in 10 ml of 0.5N HCl and water was added thereto to make the whole volume 50 ml (20 mM solution).

②Buffer solution

A 0.1M Tris-HCl buffer solution (pH 8.40) was prepared by dissolving glycylglycine so as to make the concentration 40 mmol/liter.

[Procedure]

To 50 μl of sample (serum), 2.0 ml of the buffer solution was added and incubated at 37° C. for 3 minutes, followed by addition of 0.5 ml of the substrate solution. After mixing well, an increase of absorbance at 410 nm was measured by using the spectrophotometer.

γ-GTP activity values obtained in Example 1 and Reference Example 1 of 40 samples are listed in Table 2.

TABLE 2

| Sample No. | Example 1 | Reference Example 1 | Sample No. | Example 1 | Reference Example 1 |
|---|---|---|---|---|---|
|  | mIU | mIU |  | mIU | mIU |
| 1 | 213 | 215 | 21 | 245 | 251 |
| 2 | 117 | 113 | 22 | 63 | 65 |
| 3 | 212 | 218 | 23 | 8 | 11 |
| 4 | 301 | 319 | 24 | 3 | 4 |
| 5 | 152 | 155 | 25 | 6 | 7 |
| 6 | 132 | 141 | 26 | 96 | 101 |
| 7 | 92 | 95 | 27 | 321 | 328 |
| 8 | 72 | 76 | 28 | 246 | 248 |
| 9 | 100 | 103 | 29 | 151 | 159 |
| 10 | 62 | 64 | 30 | 279 | 283 |
| 11 | 139 | 142 | 31 | 424 | 430 |
| 12 | 235 | 241 | 32 | 91 | 93 |
| 13 | 195 | 197 | 33 | 182 | 191 |
| 14 | 95 | 96 | 34 | 63 | 65 |
| 15 | 60 | 63 | 35 | 160 | 161 |
| 16 | 241 | 249 | 36 | 213 | 215 |
| 17 | 23 | 22 | 37 | 164 | 160 |
| 18 | 12 | 9 | 38 | 263 | 257 |
| 19 | 189 | 191 | 39 | 113 | 118 |
| 20 | 64 | 66 | 40 | 21 | 24 |

(Note) γ = 0.983, Y = 0.983 X-0.635

As is clear from Table 2, the measured values according to this invention have good correlation to those of the prior art acid dissolution method.

EXAMPLE 2

[Preparation of Reagent Solutions]

①Substrate buffer solution

A 0.1M Tris-HCl buffer solution (pH 8.40) was prepared by dissolving heptakis-(6-O-1,3-dihydroxypropyl)β-cyclodextrin (m=2, n=3 and x=7 in the formula (I)) so as to make the concentration 10 mmol/liter and γ-L-glutamyl-p-nitroanilide so as to make the concentration 5 mmol/liter.

② Glycylglycine solution

A 162 mmol/liter solution of glycylglycine was adjusted to pH 8.40 with sodium hydroxide.

[Procedure]

To 50 μl of sample, 2.0 ml of the substrate buffer solution was added and incubated at 37° C. for 3 minutes, followed by addition of 0.5 ml of the glycylglycine solution. After mixing well, an increase of absorbance at 410 nm was measured by using a spectrophotometer to calculate γ-GTP activity value.

The same results as obtained in Example 1 were obtained in this Example.

EXAMPLE 3

As the sample, there were used serum intentionally subjected to haemolysis (hemoglobin concentration: 100, 200, 400, 600, 800, and 1000 mg/dl) and serum of hemoglobin concentration of zero. The γ-GTP activity values were measured in the same manner as described in Example 1.

COMPARATIVE EXAMPLE 1

[Preparation of Reagent Solution]

In 800 ml of water, 3 mmol of γ-L-glutamyl-3-carboxy-4-nitroanilide, 40 mmol of glycylglycine, and 100 mmol of tris(hydroxymethyl)aminomethane were dissolved and the pH of the solution was adjusted to 9.0 with HCl. Then, the total volume was made 1 liter with water.

[Procedure]

The reagent solution in an amount of 2.5 ml was preincubated at 37° C. for 3 minutes, followed by addition of 50 μl of sample (serum). After mixing well, an increase of absorbance at 410 nm was measured by using a spectrophotometer. Results of γ-GTP activity values of Example 3 and Comparative Example 1 obtained by using the same samples are listed in Table 3.

TABLE 3

| | Hemoglobin conc. (mg/dl) | | | | | | |
|---|---|---|---|---|---|---|---|
| | 0 | 100 | 200 | 400 | 600 | 800 | 1000 |
| Example 3 | 93 mU (100%) | 93 (100%) | 92 (99%) | 90 (97%) | 90 (97%) | 88 (95%) | 88 (95%) |
| Comparative Example 1 | 99 mU (100%) | 98 (99%) | 97 (98%) | 91 (92%) | 86 (87%) | 86 (87%) | 81 (82%) |

As is clear from Table 3, the process of this invention is less influenced by the haemolysis compared with Comparative Example 1 wherein the water-soluble group is introduced into the substrate.

EXAMPLE 4

[Preparation of Reagent Solutions]

①Substrate solution

γ-L-Glutamyl-p-nitroanilide was dissolved in water so as to make the concentration 200 mmol/liter and heptakis-(2,6-di-O-hydroxyethyl)-β-cyclodextrin (m=1, n=2 and x=14 in the formula (I)) was dissolved in water so as to make the concentration 400 mmol/liter. The resulting solution contained no non-soluble material and the substrate was completely dissolved. The resulting mixture was separated into vials of each 2 ml, followed by freeze drying to give solid formulations. During the freeze drying, no deposition of precipitates was observed.

The solid formulations were dissolved in 20 ml of 0.1M Tris-HCl buffer solution (pH 8.40) at the time of use to give substrate solutions.

②Buffer solution

Glycylglycine was dissolved in 0.1M Tris-HCl buffer solution (pH 8.40) so as to make the concentration 40 mmol/liter.

[Procedure]

To 50 μl of sample (serum), 2.0 ml of the buffer solution was added and incubated at 37° C. for 3 minutes, followed by addition of 0.5 ml of the substrate solution. After mixed well, an increase of absorbance at 410 nm was measured by using a spectrophotometer.

The same results as obtained in Example 1 were obtained in this Example.

Example 5

[Preparation of Reagent Solutions]

①Substrate solution

γ-L-Glutamyl-p-nitroanilide was dissolved in water so as to make the concentration 100 mmol/liter and β-cyclodextrin-epichlorohydrin condensate [average molecular weight, about 3000; molar ratio of β-cyclodextrin to epichlorohydrin=1:2; k≈2 and i+j≈4 in the formula (II)]was dissolved in water so as to make the concentration 200 mmol/liter. The mixed solution had no non-soluble material and the complete dissolution of the substrate was observed. The mixed solution was separated into vials of each 2 ml, followed by freeze drying to give solid formulations. In this case, no deposition of precipitate was observed during the freeze drying.

The solid formulations were dissolved in 10 ml of 0.1M Tris-HCl buffer solution (pH 8.40) at the time of use to give substrate solutions.

②Buffer solution

Glycylglycine was dissolved in 0.1M Tris-HCl buffer solution (pH 8.40) so as to make the concentration 40 mmol/liter.

[Procedure]

To 50 μl of sample (serum), 2.0 ml of the buffer solution was added and preincubated at 37° C. for 3 minutes, followed by addition of 0.5 ml of the substrate solution. After mixing well, an increase of absorbance at 410 nm was measured by using a spectrophotometer so as to calculate γ-GTP activity value.

The same results as obtained in Example 1 were obtained in this Example.

As is clear from Examples 4 and 5, by using the special modified cyclodextrins, the substrate γ-L-glutamyl-p-nitroanilide can be dissolved in a large amount of 100 to 200 mmol/liter and freeze drying can be carried out more effectively.

As mentioned above, the problem of solubility of γ-L-glutamyl-p-nitroanilide in the γ-GTP activity measuring method is solved by using the special modified cyclodextrin of the formula (I) or (II). According to this invention, the following advantages are obtained:

(1) By the use of the special modified cyclodextrin, γ-L-glutamyl-p-nitroanilide is clathrated remarkably effectively to improve the substrate solubility and to improve the stability of the substrate solution after dissolution.

(2) Enzymatic activity of γ-GTP is not suppressed by such a modified cyclodextrin and measured values of γ-GTP activity can be obtained easily and quantitatively.

(3) By using the special modified cyclodextrin, the substrate solubility is increased to 150 mM or more, and the solubility at low temperatures is remarkably improved to make freeze drying of the condensed substrate solution for giving solid formulations remarkably easy.

(4) By using the special modified cyclodextrin, no deposition of precipitates and no rise of reagent blank value in the substrate solution is observed for a long period of time after the preparation.

What is claimed is:

1. A process for determining τ-glutamyl transpeptidase activity which comprises adding to a sample a substrate solution comprising τL-glutamyl-p-nitroanilide and a modified cyclodextrin of the formula:

$$\beta\text{-CD}(-\text{OH})_{21-x}[-\text{OC}_n\text{H}_{2n-(m-1)}(-\text{OH})_m]_x \quad (\text{I})$$

wherein CD is a cyclodextrin residue; m is an integer of 1 to 10; n is an integer of 1 to 5, provided that $2n-(m-1) \geq 0$; and x is 3 to 21, or a modified cyclodextrin of the formula:

$$\left[ (\text{OH})_{14-i} \underset{(\text{CH}_2\text{OH})_{7-j}}{\overset{}{\fbox{}}} \begin{array}{l} (\text{+O}-\text{CH}_2\overset{\text{OH}}{\underset{|}{\text{CH}}}\text{CH}_2)_i \\ (\text{CH}_2-\text{OCH}_2\overset{\text{OH}}{\underset{|}{\text{CH}}}\text{CH}_2)_j \end{array} \right]_k \quad (\text{II})$$

wherein i is zero to 3; j is 1 to 5; and k is 2 to 5, and adding to the sample an acceptor solution containing an acceptor for glutamic acid, in this order or a reverse order, and quantitatively measuring p-nitroaniline generated from τ-L-glutamyl-p-nitroanilide by τ-glutamyl transpeptidase activity, wherein the amount of p-nitroaniline is an indication of the activity of gamma-glutamyl-transpeptidase activity.

2. A process according to claim 1, wherein the modified cyclodextrin of the formula (I) or (II) is used in an amount of 1.2 to 5.0 moles per mole of the substrate.

3. A process according to claim 1, wherein the acceptor for glutamic acid is glycylglycine.

4. A process according to claim 1, wherein the p-nitroaniline generated is measured by using a spectrophotometer.

5. A process according to claim 1, wherein the modified cyclodextrin of the formula (II) is a β-cyclo-dextrin-epichlorohydrin condensate.

6. A process according to claim 1, wherein the modified cyclodextrin of the formula (I) is heptakis-(6-O-hydroxypropyl)-β-cyclodextrin, heptakis-(6-O-1,3-dihydroxypropyl)-β-cyclodextrin, heptakis-(2,6-di-O-hydroxyethyl)-β-cyclodextrin, or heptakis-(6-O-hydroxy- sec-butyl)-β-cyclodextrin.

7. A reagent kit for determination of γ-glutamyl transpeptidase activity comprising in separate containers;

(A) a substrate solution comprising γ-L-glutamyl-p-nitroanilide, and a modified cyclodextrin of the formula:

$$\beta-CD(-OH)_{21-x}[-OC_nH_{2n-(m-1)}(-OH)_m]_x \quad (I)$$

wherein CD is a cyclodextrin residue; m is an integer of 1 to 10; n is an integer of 1 to 5, provided that $2n-(m-1) \geq 0$; and x is 3 to 21, or a modified cyclodextrin of the formula:

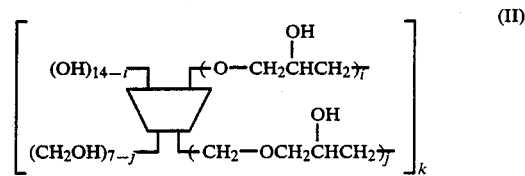

wherein i is zero to 3; j is 1 to 5; and k is 2 to 5, and (B) an acceptor solution containing an acceptor for glutamic acid.

8. A reagent kit according to claim 7, wherein the modified cyclodextrin of the formula (II) is a β-cyclodextrin-epichlorohydrin condensate.

9. A reagent kit according to claim 7 wherein the modified cyclodextrin of the formula (I) is heptakis-(6-O-hydroxypropyl)-β-cyclodextrin, heptakis-(6-O-1,3-dihydroxypropyl)-β-cyclodextrin, heptakis-(2,6-di-O-hydroxyethyl)-β-cyclodextrin, or heptakis-(6-O-hydroxy-sec-butyl)-β-cyclodextrin.

* * * * *